US00PP36475P2

(12) United States Plant Patent
Kap

(10) Patent No.: US PP36,475 P2
(45) Date of Patent: Feb. 18, 2025

(54) ***EPIPREMNUM* PLANT NAMED 'KASCIGRFL'**

(50) Latin Name: *Epipremnum aureum*
Varietal Denomination: KASCIGRFL

(71) Applicant: Kap Scindapsus B.V., Honselersdijk (NL)

(72) Inventor: Jeffrey Kap, Honselersdijk (NL)

(73) Assignee: Kap Scindapsus B.V., Honselersdijk (NL)

( * ) Notice: Subject to any disclaimer, the term of this patent is extended or adjusted under 35 U.S.C. 154(b) by 0 days.

(21) Appl. No.: 18/831,202

(22) Filed: Sep. 12, 2024

(30) Foreign Application Priority Data

Sep. 12, 2023 (QZ) ..... PBR 20231876

(51) Int. Cl.
*A01H 6/00* (2018.01)
*A01H 5/00* (2018.01)

(52) U.S. Cl.
USPC ..... Plt./373

(58) Field of Classification Search
USPC ..... Plt./373
CPC ..... A01H 6/00; A01H 5/00
See application file for complete search history.

*Primary Examiner* — Keith O. Robinson
(74) *Attorney, Agent, or Firm* — Samuel R. McCoy, Jr.

(57) ABSTRACT

A new and distinct *Epipremnum aureum* plant named 'KASCIGRFL' which is characterized by a trailing and vining habit, with glossy cordate foliage that emerges mid-green with light yellow-green marbling and blotches and matures to dark green with strong yellow-green marbling and blotching, as well as the stability of these characteristics from generation to generation.

3 Drawing Sheets

Latin name of the genus and species: The Latin name of the genus and species of the novel variety disclosed herein is *Epipremnum aureum.*

Variety denomination: The inventive variety of *Epipremnum* disclosed herein has been given the variety denomination 'KASCIGRFL'.

BACKGROUND OF THE INVENTION

Parentage: 'KASCIGRFL' is a spontaneous partial-plant branch mutation which was discovered growing amongst a cultivated population of unnamed *Epipremnum aureum* plants (not patented) that typify the species. The claimed plant was discovered by the inventor in 2020 at a commercial greenhouse near Honselersdijk, The Netherlands and was first noted for the unique mottled coloration of the juvenile foliage that contrasted with the dark green mature foliage. At that time, stem cuttings were harvested from the mutated branch, rooted, and the resulting plants grown to maturity in order to confirm the distinguishing characteristics first observed and the stability thereof. The new plant was selected for commercialization in March of 2023

Asexual Reproduction: Asexual reproduction of the new cultivar 'KASCIGRFL', by way of rooting stem cuttings, was first performed in March of 2023 at a commercial greenhouse in Honselersdijk, The Netherlands. Through eight subsequent generations, the unique features of this cultivar have proven to be stable and true to type.

SUMMARY OF THE INVENTION

The cultivar 'KASCIGRFL' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'KASCIGRFL'. These characteristics in combination distinguish 'KASCIGRFL' as a new and distinct *Epipremnum* cultivar:

1. *Epipremnum* 'KASCIGRFL' exhibits trailing and vining growth habit with glossy cordate foliage; and
2. *Epipremnum* 'KASCIGRFL' exhibits yellow-green juvenile foliage that is moderately marbled and blotched with a lighter shade of yellow-green along the lateral veins; and
3. *Epipremnum* 'KASCIGRFL' exhibits dark green mature foliage that is moderately to strongly marbled and blotched with light yellow-green along the lateral veins.

BOTANICAL DESCRIPTION OF THE PLANT

Figure 1:
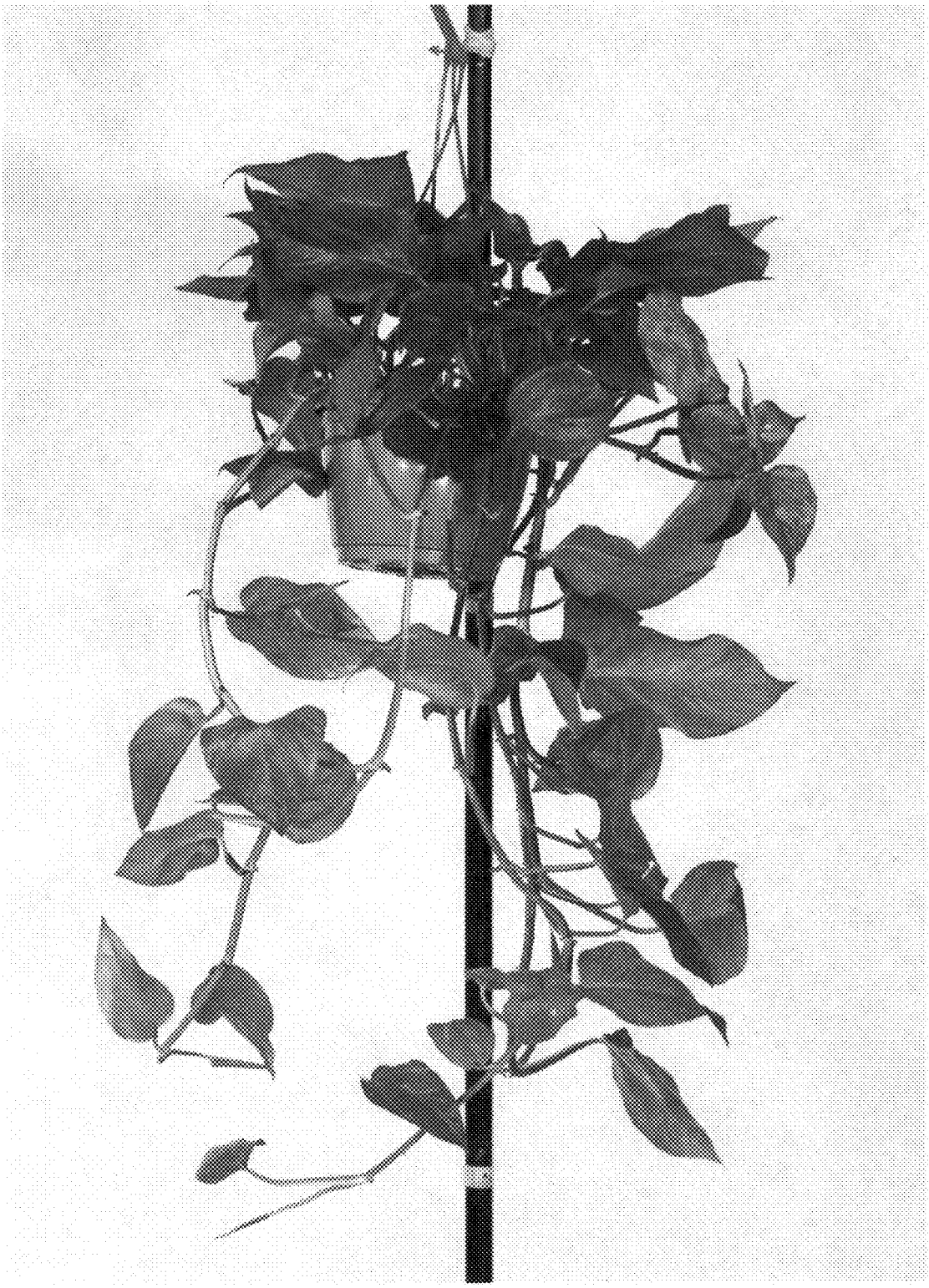
FIG. 1 illustrates, as nearly true as it is reasonably possible to make the same in color photographs of this type, an exemplary 12-month-old 'KASCIGRFL' plant in a 14 cm nursery pot, grown in a greenhouse in Honselersdijk, The Netherlands.
Figure 2:
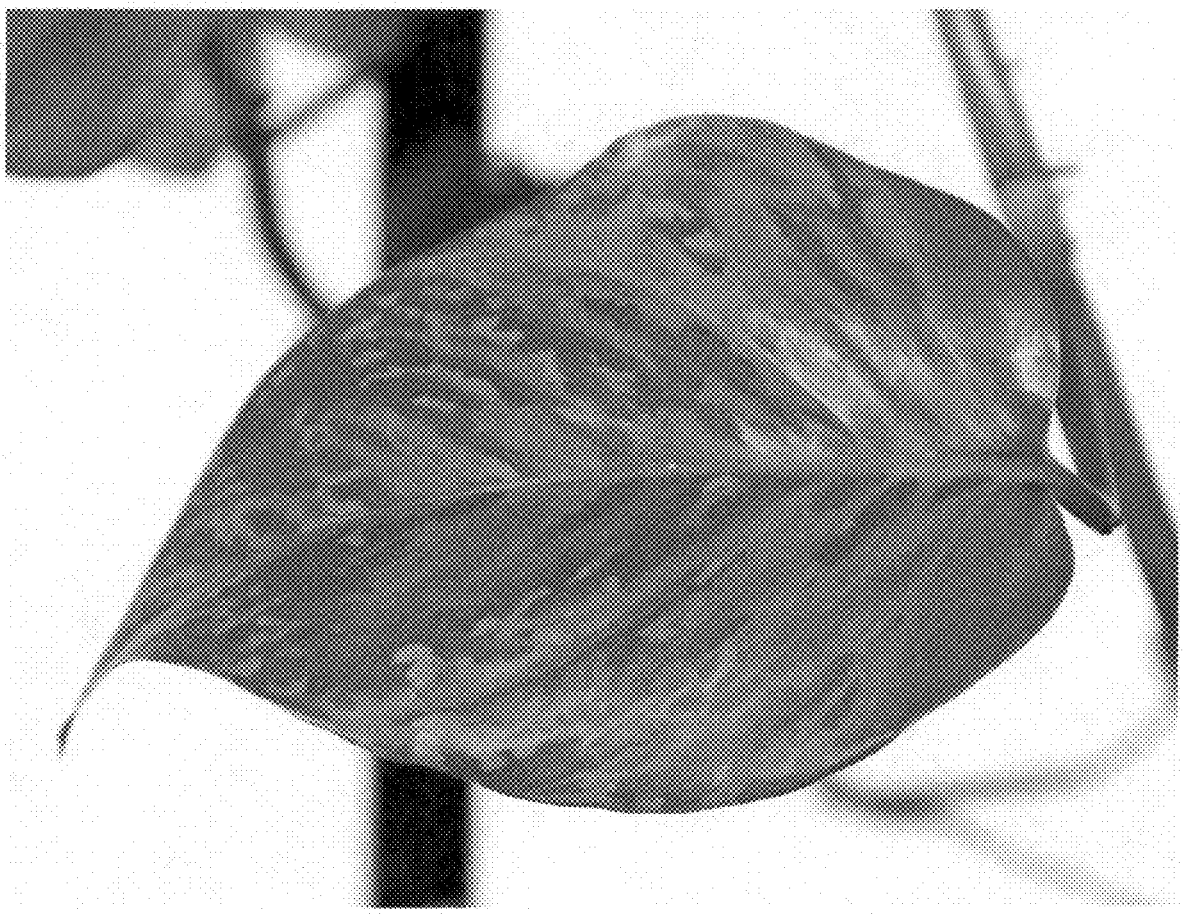
FIG. 2 illustrates, as nearly true as it is reasonably possible to make the same in color photographs of this type, the juvenile foliage of 'KASCIGRFL'.
Figure 3:
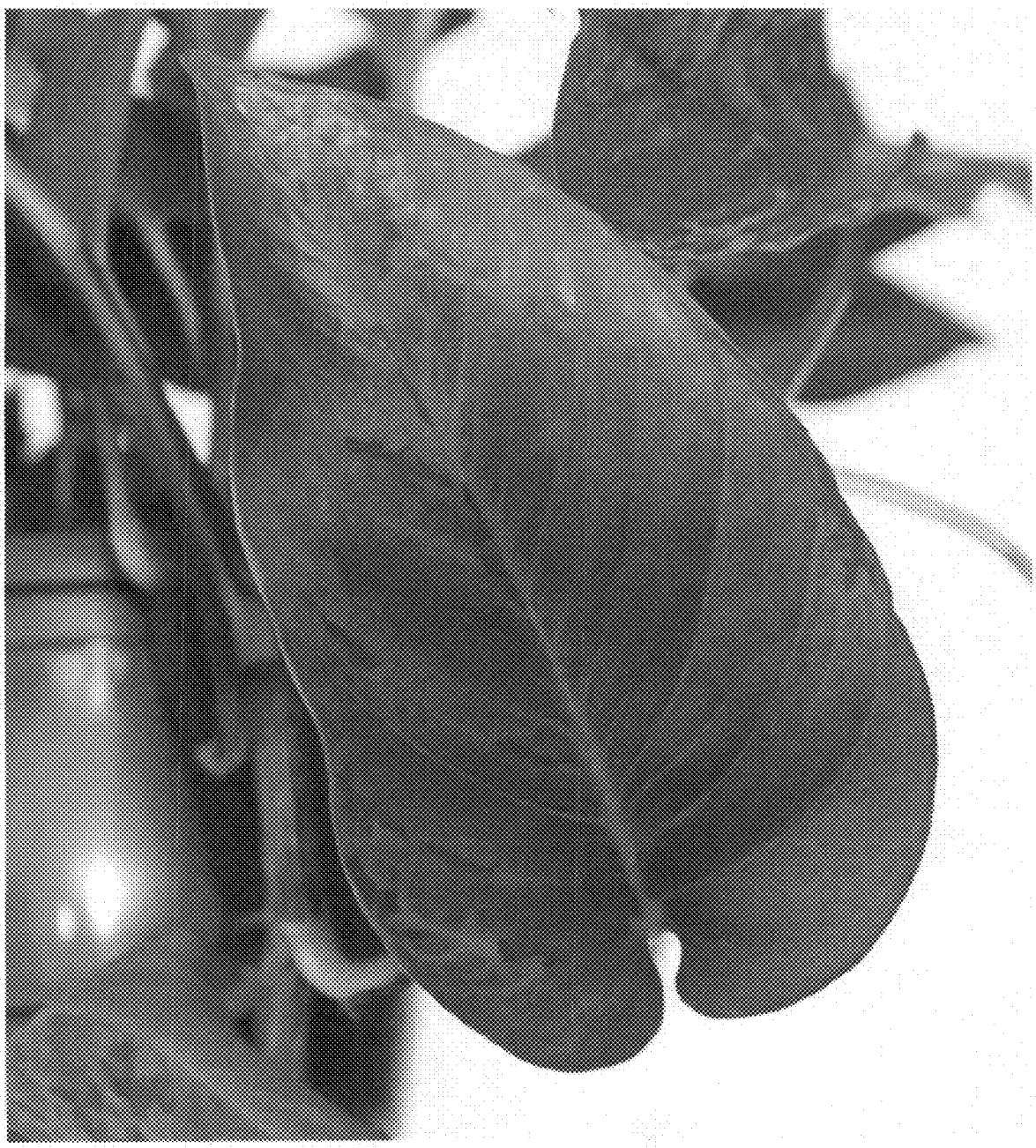
FIG. 3 illustrates, as nearly true as it is reasonably possible to make the same in color photographs of this type, the mature foliage of 'KASCIGRFL', partially obscured by juvenile foliage.

The following observations and measurements, made in January of 2024, describe a 12-month-old 'KASCIGRFL' plant. The plant was grown from a single unrooted cutting, in 14 cm nursery containers, at a commercial greenhouse near Honselersdijk, The Netherlands. The plant was produced using conventional greenhouse production protocols for *Epipremnum* sp. which entailed growing plants under heavy percent shade, regularly watering with overhead irrigation, and fertilizing with a slow-release granular fertilizer. No chemical pest measures or photoperiodic treatments were utilized during production.

Those skilled in the art will appreciate that certain characteristics will vary with older or, conversely, with younger plants. 'KASCIGRFL' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, sixth edition.

A botanical description of 'KASCIGRFL' and a comparison with the parent, which is also the most similar commercial variety of *Epipremnum aureum* known to the inventor, are provided below.

Plant description:

*Growth habit*.—Evergreen trailing and vining perennial.

*Average height from base to top of foliage*.—77 cm from the top of the floral plane to the lowest hanging stem.

*Average width*.—55.3 cm, as observed.

*Growth rate*.—Moderately fast growing.

*Plant vigor*.—Vigorous.

*Propagation method*.—Leaf cuttings; rooting is initiated in approximately 21 days, when grown in a greenhouse with an ambient average temperature of 26° C.

*Time to produce a finished plant*.—Approximately 6 weeks are required to produce a fully rooted and marketable 11 cm plant from a rooted cutting, when grown under greenhouse conditions.

*Disease and pest resistance or susceptibility*.—Plants have not been observed to be susceptible or resistant to pathogens and pests common to *Epipremnum* sp.

*Environmental tolerances*.—Adapt to at least USDA Zones 10 and 13; moderate tolerance to rain; low tolerance to wind; low tolerance to drought.

Root system:

*General*.—*Epipremnum* sp. has the propensity to produce both subterranean and aerial roots.

*Branching*.—Freely branched.

*Density*.—Moderately dense.

*Distribution*.—Subterranean roots are shallow to moderately deep. Aerial roots forming at the nodes along stems.

*Texture*.—Fleshy; smooth; lacking root hairs.

*Aerial roots*.—Approximately 0.6 cm long and 0.3 cm wide; colored greyed-brown, nearest to a combination of RHS 199B, 199C, and 199D.

Stem:

*Branching habit*.—A plurality of main stems arising directly from the base of the plant; main stems are unbranched.

*Quantity of main stems*.—7 per plant, as observed.

*Aspect*.—Terete; adaxially striated and smooth underneath.

*Length of stems*.—46.8 cm, as observed.

*Diameter of stems*.—0.7 cm at the widest point.

*Internode length*.—6.6 cm.

*Attitude*.—Prostrate; weeping, when grown in a hanging basket.

*Strength*.—Moderately strong.

*Texture and luster*.—Glabrous and slightly glossy.

*Color*.—Juvenile stems, adaxial surface — Green, nearest to RHS 143B. Juvenile stems, abaxial surface — Yellow-green, nearest to RHS 145B. Nodes, adaxial surface — Yellow-green, nearest to RHS 147A. Nodes, abaxial surface — Yellow-green, nearest to RHS 146D. Mature stems, adaxial surface — Greyed-green, nearest to in between RHS 197A and 197B. Mature stems, abaxial surface — Greyed-green, nearest RHS 197D.

Foliage:

*Arrangement*.—Alternate.

*Division*.—Simple.

*Attachment*.—Petiolate.

*Quantity of foliage*.—Average of 8 leaves per main stem.

*Lamina*.—Dimensions — 15.6 cm long and 9.1 cm wide, on average. Shape — Ovate to broad ovate. Aspect — Slightly to moderate carinate. Apex — Acuminate. Base — Cordate to hastate. Margin — Entire; coarsely undulate. Pubescence, texture and luster of adaxial surface — Glabrous, smooth, and glossy. Pubescence, texture and luster of abaxial surface — Glabrous, smooth, and moderately glossy. Color — Juvenile foliage, adaxial surface — Yellow-green, nearest to in between RHS 144A and 146A; moderately marbled and blotched along the lateral veins, nearest to RHS 145A. Juvenile foliage, abaxial surface — Yellow-green, nearest to RHS 146B; moderately marbled and blotched along the lateral veins, nearest to RHS 146D. Mature foliage, adaxial surface — Green, nearest to RHS 139A; moderately to strongly marbled and blotched along the lateral veins, nearest to RHS 145A. Mature foliage, abaxial surface — Yellow-green, nearest to RHS 146B; moderately marbled and blotched along the lateral veins, nearest to a combination of RHS 146C and 146D. Venation — Pattern — Pinnate. Mature venation color, adaxial surface — Green, nearest to RHS NN137A. Mature venation color, abaxial surface — Yellow-green, nearest to RHS 147D.

*Petiole*.—Aspect — Subterete. Length — 2.5 cm. Width — 0.6 cm. Texture — Smooth and glabrous. Luster — Slightly glossy. Strength — Moderately strong. Color — Yellow-green, nearest to a blend of RHS 145A and 147D.

*Stipules*.—General — Two long and narrow stipules are fused to the petiole; stipules desiccate as foliage matures and will eventually senesce with age. Length — 7.7 cm. Width — 0.2 cm at the base. Texture — Smooth and glabrous. Luster — Slightly glossy. Color — Greyed-green, nearest to in between RHS 192C and 192D.

Inflorescence: To date, no flowering has been observed.

Bud: To date, no flowering has been observed.

Flower: To date, no flowering has been observed.

Reproductive organs: To date, no flowering has been observed.

Seed and fruit: To date, no flowering has been observed.

Comparisons with the Parent Plant

Plants of the new cultivar 'KASCIGRFL' differ from the parent, plants of *Epipremnum aureum* which typify the species, by the characteristics described in Table 1.

TABLE 1

| Characteristic | 'KASCIGRFL' | The parent. |
|---|---|---|
| Expression of foliage variegation; variegation pattern. | Moderately to strongly marbled and blotched. | Lightly to moderately blotched. |
| General coloration of the foliage. | Green and marbled and blotched with lighter shades of yellow-green. | Mid-green with golden yellow blotches. |
| Luster of juvenile foliage. | Glossy. | Matte. |

Comparison with the Most Similar Variety Known to the Inventor

Plants of the new cultivar 'KASCIGRFL' differ from the most similar commercial variety known to the inventor, *Epipremnum aureum* 'Marble Queen' (not patented), by the characteristics described in Table 2.

TABLE 2

| Characteristic | 'KASCIGRFL' | 'Marble Queen' |
|---|---|---|
| General coloration of the juvenile foliage. | Green and marbled and blotched with light shades of yellow-green. | Green and marbled and blotched with cream white. |

That which is claimed is:

1. A new and distinct *Epipremnum aureum* plant named 'KASCIGRFL', substantially as described and illustrated herein.

* * * * *